United States Patent [19]

Triller et al.

[11] 4,329,737

[45] May 11, 1982

[54] LIGHT-EMITTING DIODE ARRANGEMENT

[75] Inventors: Adolf Triller, Munich; Helmut Gassenhuber, Söcking, both of Fed. Rep. of Germany

[73] Assignee: Optische Werke G. Rodenstock, Munich, Fed. Rep. of Germany

[21] Appl. No.: 172,951

[22] Filed: Jul. 28, 1980

[30] Foreign Application Priority Data

Jul. 26, 1979 [DE] Fed. Rep. of Germany ....... 2930383

[51] Int. Cl.$^3$ .............................................. F21V 7/04
[52] U.S. Cl. ..................................... 362/32; 362/231; 362/235; 362/249; 362/293; 362/311; 362/800; 362/804
[58] Field of Search ................. 362/32, 231, 235, 249, 362/293, 311, 800, 804

[56] References Cited

U.S. PATENT DOCUMENTS 4,097,917 6/1978 McCaslin ............................ 362/32

Primary Examiner—Stephen J. Lechert, Jr.
Attorney, Agent, or Firm—Craig and Antonelli

[57] ABSTRACT

A light-emitting diode arrangement with a light-emitting diode that is light-transmissive in an axial direction of the type used in examining instruments for opthalmic optics. The light-emitting diode serves as a constant light source in conjunction with a diffusion disk, such as for fixation point stimuli, while the disk also serves as a stimulus that is lit by an additional, switchable light source, such as an incandescent lamp, whose light is transmitted through a light guide, such as an optical fiber, through the light-emitting diode to the disk. In a preferred embodiment, a color filter is arranged between the additional light source and the light-emitting diode and both the additional light source and light-emitting diode are axially displaceable relative to the diffusion disk so as to enable adjustment of their respective luminous densities.

7 Claims, 1 Drawing Figure

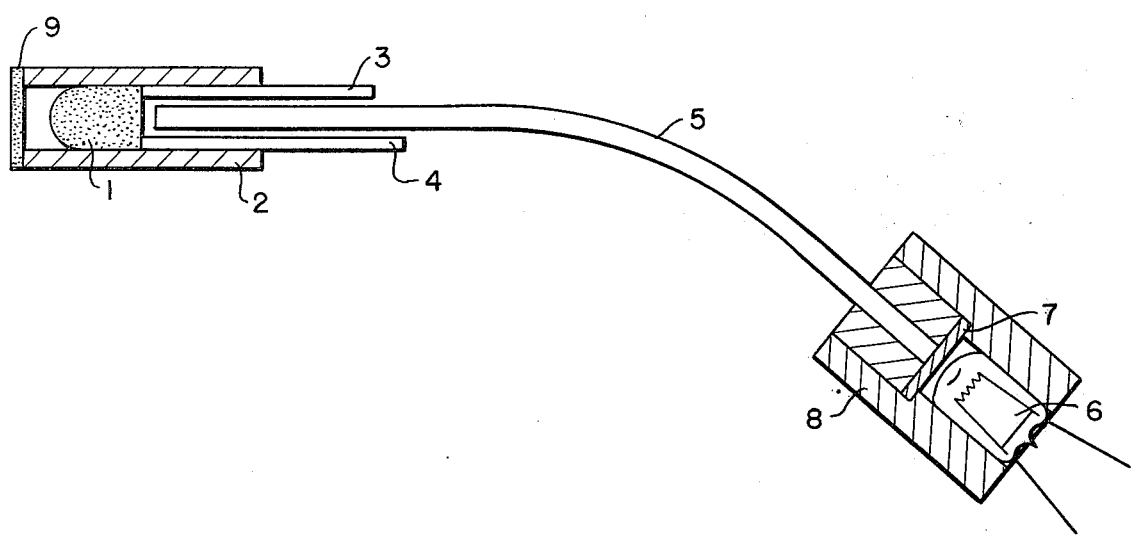

LIGHT-EMITTING DIODE ARRANGEMENT

BACKGROUND AND SUMMARY OF THE INVENTION

The invention relates to a light-emitting diode arrangement with a light-emitting diode that is light-transmissive in an axial direction, preferably for use in examining instruments for ophthalmic optics.

It is known from German Pat. Nos. 2,507,723 and 2,552,839 to utilize light-emitting diodes as the stimuli in perimetric eye examining instruments. Such instruments comprise, besides a plurality of stimuli lit up briefly in various groupings, one or selectively several targets as fixation points which are constantly lit up during the course of the examination.

It is an object of the invention to provide an arrangement usable as a stimulus as well as in the form of a fixation target. In this connection, it is a prerequisite that the light-emitting diodes used as the stimuli exhibit a luminous density [luminance] which is, to a high degree, the same for all of the diodes; the light sources employed as fixation targets are to differ considerably in color and brightness from the stimuli.

Due to the two last-mentioned criteria, light-emitting diodes permitting a color switchover by electronic means are unsuitable for the purpose contemplated herein.

According to a preferred embodiment of the invention, the above-noted object can be attained by combining a light-emitting diode with an additional, switchable light source, the switchable light source penetrating the light-emitting diode from its rear face toward its light-emtting side.

The arrangement of this invention can be used not only in perimetric eye examining instruments, but also in all cases where an indicator light is to be lit up on an intermittently different color and brightness.

These and further objects, features and advantages of the present invention will become more obvious from the following description when taken in connection with the accompany drawings which show, for purposes of illustration only a single embodiment in accordance with the present invention.

BRIEF DESCRIPTION OF THE DRAWING

The sole FIGURE is a cross-sectional view of a preferred embodiment of the invention.

DETAILED DESCRIPTION OF THE PREFERRED EMBODIMENT

The light-emitting diode 1 is arranged in a sleeve 2 intended for being attached to the usage site. Terminals 3 and 4 serve for supplying current to the light-emtting diode 1. A lightguide 5, which may be an optical fiber, leads from the incandescent lamp 6 to the light-emitting diode 1. A color filter 7 is disposed between the light entrance end of the lightguide 5 and the incandescent lamp 6.

The incandescent lamp can also cooperate with several light-emitting diodes by way of several lightguides.

It is also possible to connect the sleeve 2 of the light-emitting diode 1 to the socket 8 of the incandescent lamp 6 without the interposition of the lightguide 5. For this purpose, the terminals 3 and 4 of the light-emitting diode 1 would have to be extended laterally out of the sleeve 2.

The sleeve 2 can be closed off at its light-emitting end by a diffusion disk 9. By a longitudinal displacement of the light-emitting diode 1 in the sleeve 2, the luminous density effective at the diffusion disk 9 can be adjusted. A similar adjustment is possible by a longitudinal displacement of the incandescent lamp 6 in the socket 8.

Accordingly, it can be seen that the arrangement according to the present invention enables a first indicator light constantly produced by the diode 1 to be visible at disk 9 for use as a fixation target while also enabling a second indicator light of a considerably different color and brightness, intermittently produced and transmitted through the diode 1 from light source 6, to be visible at disk 9.

While we have shown and described one embodiment in accordance with the present invention, it is understood that the same is not limited thereto but is susceptible of numerous changes and modifications as known to those skilled in the art and we therefore do not wish to be limited to the details shown and described therein but intend to cover all such changes and modifications as incompassed by the scope of the impending claims.

What is claimed is:

1. Light-emitting diode arrangement with a light-emitting diode that is light-transmissive in an axial direction, for use in examining instruments for ophthalmic optics, characterized in that the light-emitting diode is combined with an additional, switchable light source, the light of which penetrates the light-emitting diode from its rear face toward its light-emitting side.

2. Arrangement according to claim 1, characterized in that the additional light source is an incandescent lamp.

3. Arrangement according to claim 1, characterized in that a color filter is arranged between the additional light source and the light-emitting diode.

4. Arrangement according to claim 1, characterized in that a lightguide is disposed between the additional light source and the light-emitting diode.

5. Arrangement according to claim 1, characterized in that the light-emitting diode is disposed to be longitudinally displaceable in a sleeve that is sealed at the light-emitting side of the diode with a light diffusion disk.

6. Arrangement according to claim 1, characterized in that the additional light source is disposed to be displaceable in its socket in the axial direction relative to the light-emitting diode.

7. Arrangement according to claim 1, characterized in that the additional light source is disposed to be displaceable in its socket in the axial direction relative to entrance end of the lightguide.

* * * * *